United States Patent [19]

Imai

[11] 4,070,413
[45] Jan. 24, 1978

[54] DEHYDROGENATION OF SATURATED HYDROCARBONS

[75] Inventor: Tamotsu Imai, Mount Prospect, Ill.

[73] Assignee: UOP Inc., Des Plaines, Ill.

[21] Appl. No.: 736,281

[22] Filed: Oct. 28, 1976

[51] Int. Cl.² .................................................. C07C 5/36
[52] U.S. Cl. .............................. 260/683.3; 260/666 A; 252/466 PT; 252/474
[58] Field of Search .......................... 260/683.3, 666 A

[56] References Cited
U.S. PATENT DOCUMENTS

| | | | |
|---|---|---|---|
| 2,620,314 | 12/1952 | Hoekstra | 252/448 |
| 3,856,870 | 12/1974 | Hayes | 260/668 D |
| 3,939,220 | 2/1976 | Rausch | 260/668 D |

*Primary Examiner*—Veronica O'Keefe
*Attorney, Agent, or Firm*—James R. Hoatson, Jr.; Robert W. Welch; William H. Page II

[57] ABSTRACT

Paraffinic hydrocarbons are dehydrogenated in contact with a catalytic composite comprising from about 0.01 to about 2.0 wt. % Group VIII metal and from about 0.01 to about 0.1 wt. % lithium impregnated on an alumina support, said alumina having been hydrothermally treated in steam at a temperature of from about 800° to about 1200° C.

11 Claims, No Drawings

DEHYDROGENATION OF SATURATED HYDROCARBONS

The present invention relates to the dehydrogenation of saturated hydrocarbons. More specifically, the present invention relates to a catalytic process for the dehydrogenation of saturated hydrocarbons, and is particularly directed to the dehydrogenation of paraffinic hydrocarbons. The process of this invention affords an improvement in the conversion of saturated hydrocarbons, and an improvement in the conversion, that is, selectivity, of said hydrocarbons to the corresponding monoolefinic hydrocarbons.

The present invention is particularly applicable to a process for the dehydrogenation of propane, butane, isobutane, pentane, isopentane, and various paraffinic hydrocarbons containing six or more carbon atoms per molecule, all of which can be successfully dehydrogenated to form the corresponding olefinic hydrocarbon. In many instances, with certain modifications which will be apparent to those skilled in the art, cycloparaffins may be dehydrogenated to form the corresponding cycloolefins.

The olefinic hydrocarbon products of the process of this invention are useful in themselves, but more often as an intermediate in the manufacture of other and more valuable products. For example, propylene is extensively employed in the manufacture of polypropylene, isopropyl alcohol, cumene, isoprene, glycerol, propylene oxide, and propylene dimer, trimer and tetramer; butene-1 as well as cis- and trans-butene-2 are useful in the production of polymer and alkylate gasolines, polybutene, butadiene, and as intermediates in the manufacture of $C_4$ and $C_5$ oxides, aldehydes and ketones; and the pentenes are generally useful in organic synthesis, with pentene-1 being particularly useful as a blending agent for high octane motor fuels. The higher molecular weight monoolefins, for example, hexene, heptene, octene, nonene, decene, and the like, are useful in organic synthesis, especially in the manufacture of perfumes, flavors, dyes, pharmaceuticals, etc., those in the $C_{10}$–$C_{18}$ range being particularly useful in the production of biodegradable detergents or surfactants.

A commercially acceptable dehydrogenation process will invariably require the aid of a suitable dehydrogenation catalyst. While the endothermic dehydrogenation reaction can be effected on a strictly thermal basis, the extremely high temperatures required to attain any substantial degree of dehydrogenation also effect a substantial degree of thermal cracking, and the product yield as well as the product quality is accordingly adversely affected.

It is an object of this invention to present a novel and improved process for the catalytic dehydrogenation of saturated hydrocarbons. One of the more specific objects is to provide a catalytic process of improved activity and activity stability with respect to the conversion of paraffinic hydrocarbons, and of improved selectivity and selectivity stability with respect to the conversion of said paraffinic hydrocarbons to the corresponding monoolefinic hydrocarbons.

The prior art concerning the dehydrogenation of saturated hydrocarbons makes reference to any number of catalysts suitable for promoting the relatively low temperature conversion of said hydrocarbons to olefinic products. Of the numerous catalysts which have been proposed, those comprising a Group VIII metal component and lithium on an alumina support or carrier material are among the more prominent, and the state of the art has become well developed with respect thereto. However, as those familiar with the art of catalysis are well aware, even minor variations in composition and/or methods of manufacture can, and often do, effect a significant and unanticipated improvement in the activity, selectivity and/or stability of a catalyst product with respect to one or more hydrocarbon conversion reactions.

Thus, pursuant to one embodiment of the present invention for the dehydrogenation of a saturated hydrocarbon, improved conversion as well as selectivity is achieved when said hydrocarbon is contacted with a catalytic composite at dehydrogenation reaction conditions including a temperature of from about 400° to about 700° C., said catalytic composite comprising from about 0.01 to about 2.0 wt. % Group VIII metal and from about 0.01 to about 0.1 wt. % lithium impregnated on an alumina support, said alumina having been hydrothermally treated in steam at a temperature of from about 800° to about 1200° C.

Other objects and embodiments will become apparent in the following detailed specification.

The catalytic composite employed in the dehydrogenation process of this invention comprises a Group VIII metal component, an alkali metal or alkaline earth metal component and an alumina support or carrier material, and said catalytic composite may be prepared in any conventional or convenient manner provided that said support or carrier material is subjected to the hydrothermal treatment herein described.

Thus, the alumina component of said composite may be derived from any suitable alumina source including naturally occurring and synthetically prepared aluminas, provided that the selected alumina is in any case further hydrothermally treated in steam at a temperature of from about 800° to about 1200° C. The alumina source may therefore be any of the various hydrous aluminum oxides or gels, including alpha-alumina monohydrate (boehmite), alpha-alumina trihydrate (gibbsite), beta-alumina trihydrate (bayerite), and the like. Aluminas which have been thermally treated to eliminate substantially all of the water and/or hydroxyl groups commonly associated therewith, are particularly suitable precursors of the alumina component employed herein, especially gamma-alumina and eta-alumina resulting from the thermal treatment of boehmite and bayerite alumina respectively, generally at a temperature of from about 400° to about 850° C.

The alumina precursor of the alumina component of the catalytic composite will typically be employed in a particle size and shape dictated by the desired size and shape of the final catalytic composite, e.g., spheres, pills, pellets, granules, extrudates, etc. Spheroidal alumina particles are frequently preferred, and spheroidal gamma-alumina particles, particularly responsive to the hydrothermal treatment herein contemplated, are advantageously prepared by the oil-drop method substantially as described in U.S. Pat. No. 2,620,314. Briefly, the method comprises the preparation of an alumina sol, preferably an aluminum chloride sol such as is formed by digesting aluminum in hydrochloric acid under controlled conditions, and the dispersion of said sol as droplets in a hot oil bath whereby gelation occurs with the formation of spheroidal gel particles. In this type of operation, the alumina is set chemically utilizing ammonia as a neutralizing or setting agent. Usually, the ammonia is furnished by an ammonia precursor included in the sol, most often urea and/or hexamethylenetetramine. Only a fraction of the ammonia precursor is hydrolyzed or decomposed in the relatively short period during which the initial gelation occurs. During the subsequent aging process, the residual ammonia precursor retained in the spheroidal particles continues to decompose and effect further polymerization of the alumina whereby desirable pore characteristics of the material are established. The alumina particles are aged, usually for about 24 hours, at a temperature of from about 50° to about 105° C. and at a predetermined pH. The spheres are subsequently washed, dried and calcined at a temperature of from about 425° to about 815° C.

In any event, the alumina is further hydrothermally treated in steam at a temperature of from about 800° to about 1200° C. The alumina is suitably treated in air containing from about 5 to about 50 vol. % steam. The alumina is preferably treated in air containing from about 20 to about 40 vol. % steam at a temperature of from about 900° to about 1100° C.

The Group VIII metal component of the catalytic composite comprises from about 0.01 to about 2.0 wt. % thereof. The Group VIII metal component may be composited with the alumina by impregnation and/or ion exchange of the alumina support or carrier material with a suitable Group VIII metal compound, that is, a suitable compound of iron, nickel, cobalt, platinum, palladium, rhodium, ruthenium, osmium or iridium. Although the invention is directed to the use of a catalytic composite comprising a Group VIII metal component, the platinum group metals of Group VIII, for example, platinum, palladium, ruthenium, rhodium, osmium and iridium, are preferred. The Group VIII metal component is suitably composited with the alumina support or carrier material utilizing impregnation and/or ion-exchange techniques commonly practiced in the art. For example, in one preferred embodiment wherein the platinum group metal is platinum, alumina particles are suspended, dipped, soaked, or otherwise immersed in a solution of a soluble platinum compound. Suitable compounds include platinum chloride, chloroplatinic acid, ammonium chloroplatinate, dinitrodiaminoplatinum, and the like. It is a common practice to impregnate an alumina support or carrier material with an aqueous chloroplatinic acid solution to facilitate an even and uniform distribution of the platinum component on the alumina surface, and the resulting composite will in this and similar cases invariably contain combined halogen, although said halogen will generally be less than about 1.5 wt. % of the catalytic composite.

The catalytic composite further comprises from about 0.01 to about 0.01 wt. % alkaline earth metal or alkali metal as a component thereof. The alkaline earth or alkali metal component is such as has been commonly employed as a component of the hydrogenation catalyst to inhibit undesirable side reactions and to suppress the inherent cracking activity of platinum-containing catalysts at dehydrogenation reaction conditions. While alkaline earth metals including calcium, magnesium, and/or strontium are suitable, the alkali metals, potassium, sodium, and especially lithium, are preferred. In any case, the alkaline earth metal component or alkali metal component, can be composited with the alumina support or carrier material as an aqueous solution of a soluble compound thereof, e.g., as a chloride, sulfate, nitrate, acetate, etc., and preferably as a common aqueous solution with a Group VIII metal component.

The catalytic composite of this invention may in some cases advantageously comprise one or more components supplementing the inhibiting effect of the alkali metal or alkaline earth metal component. In particular, the catalytic composite may, in some cases, advantageously comprise a germanium, tin and/or lead component, with tin being preferred. Said components are effective inhibitors to suppress the activity of platinum-containing catalysts with respect to the isomerization and cracking of a paraffinic feed stock at dehydrogenation reaction conditions. Said components, especially tin, are effective when employed in an atomic ratio with platinum of from about 0.5 to about 2.0.

In some cases, the dehydrogenation process will be benefited by sulfiding the catalytic composite prior to use. The sulfiding is generally effected in the presence of hydrogen utilizing a sulfur-containing compound such as hydrogen sulfide, or lower molecular weight mercaptans or organic sulfides, as the sulfiding agent. Typically, the sulfiding process comprises treating the catalytic composite with a gaseous mixture of hydrogen and hydrogen sulfide in about a 100:1 mole ratio for a time, and at a temperature in the range of about 10° to about 600° C., sufficient to incorporate from about 0.05 to about 0.5 wt. % sulfur in the catalytic composite, calculated on an elemental basis.

The dehydrogenation of paraffinic hydrocarbons in contact with the catalytic composite of this invention typically comprises a continuous type of operation. Thus, the paraffinic hydrocarbon is continuously charged and passed in contact with the catalytic composite at a liquid hourly space velocity (LHSV) of from about 1.0 to about 100.0. The dehydrogenation reaction is effected in a hydrogen atmosphere at a pressure of from about 0 to about 100 psig., preferably at a pressure of from about 10 to about 50 psig. The hydrogen, principally recycle hydrogen, is charged in contact with the catalytic composite in admixture with the paraffinic hydrocarbon to provide from about 1.0 to about 20.0 moles of hydrogen per mole of hydrocarbon. Dehydrogenation reaction conditions further include a temperature of from about 400° to about 700° C., although it is preferred to operate within the more limited temperature range of from about 450° to about 550° C.

The following examples are presented in illustration of one preferred embodiment of this invention, and are not intended as an undue limitation on the generally broad scope of the invention as set out in the appended claims.

EXAMPLE I

Precalcined spheroidal gamma-alumina particles having an average bulk density of 0.3 grams per cubic centimeter and averaging about 1/16 inch in diameter, were impregnated with 0.0831 wt. % platinum and 0.056 wt. % tin from a common aqueous solution of chloroplatinic acid and stannic chloride. Precalcination of the alumina spheres was effected in flowing air at a temperature of about 525° C. over about a 2 hour interval. Impregnation was by tumbling the spheres in the solution in a rotary steam evaporator or dryer, while evaporating the solution to dryness. The impregnated spheres were subsequently calcined in air containing 30% steam for 2 hours at about 525° C. The calcined spheres were impregnated with 0.1 wt. % lithium from an aqueous solution of lithium nitrate, and further calcined in air for 2 hours at about 525° C. The resulting catalytic composite is hereinafter referred to as Catalyst A.

EXAMPLE II

A catalytic composite was prepared substantially as described in Example I except that, in accordance with this invention, the precalcined alumina spheres were subjected to a hydrothermal treatment. In this instance, the precalcined alumina spheres were heated at 1050° C. for 2 hours in flowing air containing about 35 vol. % steam. The hydrothermally treated alumina spheres were then impregnated with 0.0803 wt. % platinum, 0.0537 wt. % tin and 0.02 wt. % lithium as described, and the impregnated spheres were calcined in air containing about 30% steam for 2 hours at 525° C., and for 2 hours in air at 525° C. The resulting catalytic composite is hereinafter referred to as Catalyst B.

EXAMPLE III

The catalytic composite of this example is substantially as described in the previous example except that it comprises 0.141 wt. % platinum, 0.094 wt. % tin, and 0.038 wt. % lithium. The final catalytic composite, designated as Catalyst C, had an average bulk density of 0.305 g/cc.

The above-described catalysts were evaluated with respect to the dehydrogenation of n-heptane. The catalyst was in each case disposed as a fixed bed in a vertical tubular reactor having ½ inch diameter catalyst bed, the catalyst bed being preceded by a spiral preheat section. Normal heptane, containing about 2000 ppm. water, was charged downflow at a LHSV of 21.3 in admixture with hydrogen to provide a hydrogen/hydrocarbon mole ratio of about 4. The pressure was regulated at 30 psig. The reactor temperature was maintained at 510° C. for a 44 hour period, then at 520° C. for a 48 hour period, and at 530° C. for a 32 hour period. The reactor temperature was then reduced to the original 510° C. temperature and maintained at said temperature for a period of 24 hours. After each of said periods, the reactor effluent was sampled to determine the conversion of the n-heptane charge stock, and selectivity with respect to the formation of n-heptene. The results are set out in Table I below.

TABLE I

| Catalyst | A | B | C |
|---|---|---|---|
| platinum, wt. % | 0.0831 | 0.0803 | 0.141 |
| lithium, wt. % | 0.1 | 0.02 | 0.038 |
| tin, wt. % | 0.056 | 0.054 | 0.094 |
| ABD, gms/cc | 0.283 | 0.309 | 0.305 |
| SA, m²/gm | 167 | 63 | 63 |
| PV, cc/gm | 0.4 | 0.09 | 0.08 |
| Conversion of n-heptane, %: | | | |
| at 510° C. | 12.2 | 13.3 | 14.1 |
| at 520° C. | 13.1 ↓ 11.4 | 16.2 | 17.2 |
| at 530° C. | 12.5 ↓ 10.9 | 18.2 ↓ 17.4 | 19.7 ↓ 18.8 |
| at 510° C. | 7.8 | 12.4 | 13.2 |
| Selectivity for n-heptene (and n-heptadiene), mol %: | | | |
| at 510° C. | 88.9(4.1) | 90.6(3.5) | 90.5(3.5) |
| at 520° C. | 87.1(4.0) | 86.3(5.5) | 87.3(5.5) |
| at 530° C. | 83.4(5.4) | 83.9(6.0) | 84.3(6.7) |
| at 510° C. | 89.6(3.2) | 90.9(3.3) | 91.1(3.6) |
| Selectivity for C₇ non-normals (and toluene), mol %: | | | |
| at 510° C. | 5.9(2.6) | 5.0(2.5) | 4.7(2.9) |
| at 520° C. | 7.5(4.3) | 6.6(4.0) | 5.7(4.5) |
| at 530° C. | 9.3(6.5) | 8.4(5.9) | 7.5(6.6) |
| at 510° C. | 5.9(2.7) | 4.7(2.5) | 4.1(2.6) |
| Selectivity for light hydrocarbons, mol % | | | |
| at 510° C. | 0.9 | 0.8 | 1.1 |
| at 520° C. | 1.1 | 1.1 | 1.3 |
| at 530° C. | 1.7 | 1.5 | 1.5 |
| at 510° C. | 0.9 | 0.8 | 0.9 |

The above-tabulated data clearly demonstrate the improvements realized in the practice of this invention. Catalysts B and C, each comprising an alumina base hydrothermally treated pursuant to the present invention, exhibit an improved activity at 510°, 520° and 530° C., over that of Catalyst A with respect to the conversion of n-heptane, and also an improvement in activity stability at 510° after 148 hours onstream. Catalysts B and C also exhibit an improved selectivity at 510° C. over that of Catalyst A with respect to the conversion of n-heptane to n-heptene.

I claim as my invention:

1. A process for dehydrogenating a paraffinic hydrocarbon which comprises contacting said hydrocarbon at dehydrogenation reaction conditions including a temperature of from about 400° to about 700° C. with a catalytic composite of from about 0.01 to about 2.0 wt. % Group VIII metal component and from about 0.01 to about 0.1 wt. % of an alkali metal or alkaline earth metal component with a precalcined alumina support which has been hydrothermally treated with steam at a temperature of from about 800° to about 1200° C. after its calcination and prior to the compositing of said metal components therewith.

2. The process of claim 1 further characterized in that said catalytic composite contains a tin component in from about a 0.5:1 to about a 2:1 atom ratio with a Group VIII metal component thereof.

3. The process of claim 1 further characterized in that said hydrothermal treatment comprises heating said alumina support in an atmosphere comprising from about 5 to about 50 vol. % steam at a temperature of from about 800° to about 1200° C.

4. The process of claim 1 further characterized in that said hydrothermal treatment comprises heating said alumina support in an atmosphere comprising from about 20 to about 40 vol. % steam at a temperature of from about 900° to about 1100° C.

5. The process of claim 1 further characterized in that said Group VIII metal is a metal of the platinum group of Group VIII.

6. The process of claim 1 further characterized in that said Group VIII metal is platinum.

7. The process of claim 1 further characterized in that said hydrothermally treated alumina support is, prior to said treatment, a gamma-alumina support.

8. The process of claim 1 further characterized in that said hydrothermally treated alumina support is, prior to said treatment, a gamma-alumina support characterized by an ABD of from about 0.25 to about 0.45 grams per cubic centimeter.

9. The process of claim 1 further characterized in that said paraffinic hydrocarbon contains from about 3 to about 18 carbon atoms.

10. The process of claim 1 further characterized in that said paraffinic hydrocarbon is n-heptane.

11. The process of claim 1 further characterized in that said paraffinic hydrocarbon is n-decane.

* * * * *